US005496259A

United States Patent [19]

Perkins

[11] Patent Number: 5,496,259
[45] Date of Patent: Mar. 5, 1996

[54] STERILE PROTECTIVE SHEATH AND DRAPE FOR VIDEO LAPAROSCOPE AND METHOD OF USE

[75] Inventor: Jeffrey Perkins, Tully, N.Y.

[73] Assignee: Welch Allyn, Inc., Skaneateles Falls, N.Y.

[21] Appl. No.: 119,377

[22] Filed: Sep. 13, 1993

[51] Int. Cl.[6] .......................................... A61B 1/00
[52] U.S. Cl. ........................ 600/124; 600/121; 600/125
[58] Field of Search ................................. 128/4, 6, 844, 128/917, 918, 919; 604/263; 600/121, 122, 124, 125

[56] References Cited

U.S. PATENT DOCUMENTS

| | | | |
|---|---|---|---|
| 4,877,033 | 10/1989 | Seitz, Jr. .................................. | 128/4 X |
| 4,878,485 | 11/1989 | Adair ...................................... | 128/6 |
| 5,168,803 | 12/1992 | Kurtzer .................................... | 128/4 |
| 5,198,894 | 3/1993 | Hicks ...................................... | 128/4 X |
| 5,237,984 | 8/1993 | Williams, III et al. ...................... | 128/4 |
| 5,301,657 | 4/1994 | Lafferty et al. ............................ | 128/6 |

Primary Examiner—Richard J. Apley
Assistant Examiner—Beverly M. Flanagan
Attorney, Agent, or Firm—Harris Beach & Wilcox

[57] ABSTRACT

A sheath or cover for a laparoscope insertion tube comprises a generally rigid cylindrical wall with a face plate disposed at its distal tip. A grip mechanism at the proximal end of the rigid cylindrical wall is twisted to grip the insertion tube when the sheath is slipped onto it. An elongated tubular drape is formed of a flexible membrane, such as polyethylene film, which is folded back and forth axially on the sheath. A distal end of the drape is attached to the grip mechanism, and a proximal end is bonded to a rigid or semi-rigid tubular oversleeve. The drape is extended proximally for surgery to cover the handle and umbilical of the laparoscope. After the surgical procedure the drape is extended distally. This uncovers the umbilical and handle as well as the grip mechanism, and covers the rigid cylindrical wall of the sheath. This also inverts the drape so that all contaminated surfaces are facing inward.

7 Claims, 2 Drawing Sheets

STERILE PROTECTIVE SHEATH AND DRAPE FOR VIDEO LAPAROSCOPE AND METHOD OF USE

BACKGROUND OF THE INVENTION

This invention relates to a protective sheath for use with laparoscope, and is more particularly concerned with a sterile sheath for a laparoscope that contains an imaging device in the distal tip of its insertion tube, and carries a fiber optic bundle or similar illuminating means that emits light from the distal tip of the insertion tube.

A laparoscope is a device for observing the inside of a body cavity and permits surgical techniques to be carried out in a minimally invasive manner, i.e., through a small slit or incision in the patient.

The laparoscope has an insertion tube, which is generally a rigid elongated member that contains a miniature video camera or other imaging device at its distal end, and also contains a fiber optic bundle which carries illumination forward to illuminate a target within the patient's body cavity.

Because the surfaces that contact the patient must be completely sterile, a sterile sheath can fit over the insertion tube to isolate the insertion tube itself from contact with the patient.

One proposal for a disposable protective sheath is described in U.S. Pat. No. 4,741,326, where the sheath has the form of a flexible envelope that unwraps or unfolds over the probe tube. Another cover for an endoscope device is described in U.S. Pat. No. 5,154,164. An instrument cover of elongated cylindrical design is described in U.S. Pat. No. 4,886,049. A heat sterilizable rigid cylindrical sheath is described in U.S. Pat. No. 4,878,485.

In copending patent application Ser. No. (Attorney Docket No. 286 P 014), assigned to the assignee of this application, it is recognized that the light emitted from the illumination fiber optic bundle can reflect and scatter on surfaces of the sheath face plate. This can cause undesired flare in the optical or video image, and can impair image quality.

Contamination of the instrument can occur because of the patient's body fluids. These can contact not only the insertion tube, but also the handle, umbilical, and even the modular plug that couples the probe to a light box, monitor or other equipment. Accordingly, the sheath should include means to shield the entire probe from contamination. On the other hand, the disposable sheath should be configured in a way that minimizes risk of exposure of the health care or surgical workers to the surfaces contaminated by body fluids when the disposable sheath is removed after surgery.

A sterilizable sheath that includes an accordion-folded expandable portion is described in Adair U.S. Pat. No. 4,878,485. The expandable portion is an elastomeric material bonded to the rigid tubular part of the sheath and is intended to be pulled back to cover the flexible cord, or umbilical, of the instrument, and is retracted after surgery for removal from the probe insertion tube.

However, the accordion-folded portion always has the same side exposed to the outside, such that when the sheath is removed after a surgical procedure, the surface contaminated by contact with the patient's body fluids is still on the outside. This presents to the surgeon, nurse, and other clinical and hospital workers a significant risk of contact with these fluids.

OBJECTS AND SUMMARY OF THE INVENTION

It is an object of this invention to provide an improved sheath that avoids the drawbacks of the prior art.

It is another object to provide a sterile sheath which minimizes risk of contact with surfaces contaminated by a patient's body fluids during surgery.

In accordance with an aspect of this invention a sterile sheath is provided for the insertion tube of a laparoscope. The sheath has a cylindrical tubular wall, e.g. of stainless steel, with an inside diameter slightly greater than the outer diameter of the laparoscope insertion tube, so that it slidably fits over the same. The sheath has a generally transparent face plate at its distal end, through which the camera or optical imager views the object to be inspected or diagnosed, and from which the illumination optical fibers emit light. The tubular walls of the sterile sheath can be made of other materials, and can be constructed either for one-time use or for sterilization and reuse.

The sheath also has a tubular drape formed of a flexible film material, such as polyethylene, attached to the proximal side of the sheath tubular wall. A proximal end of this tubular drape can be attached to a cylindrical or frustoconic rigid oversleeve. The drape is folded back and forth axially.

On installation, the oversleeve is pulled back to cover the probe handle and umbilical as far back as the plug or connector module. After surgery, the oversleeve is pulled forward. This exposes the umbilical and handle, and at the same time covers the rigid tubular wall and end plate. Removal in this fashion reverses the entire flexible drape, i.e., turns it inside out. Thus, after surgery, the contaminated surfaces are all on the inside with uncontaminated, clean surfaces only on the outside. Thus, risk of exposure to contamination is minimized.

In a preferred version, a friction clamp is provided at the proximal end of the sheath for securing onto the insertion tube. This friction clamp includes a tightening system that releasably grips the insertion tube. A ring on the forward or distal side of the clamp can secure the front or distal end of the drape to the rigid cylindrical wall. If a heat sterilizable material is used in the sheath rigid wall, then the contaminated drape can be removed prior to sterilization and can be replaced by a fresh, sterile drape after :sterilization.

The above and many other objects features and advantages of this invention will become apparent from the ensuing description of a preferred embodiment, to be read in conjunction with the accompanying drawing.

DETAILED DESCRIPTION OF THE PREFERRED EMBODIMENT

Figure 1:
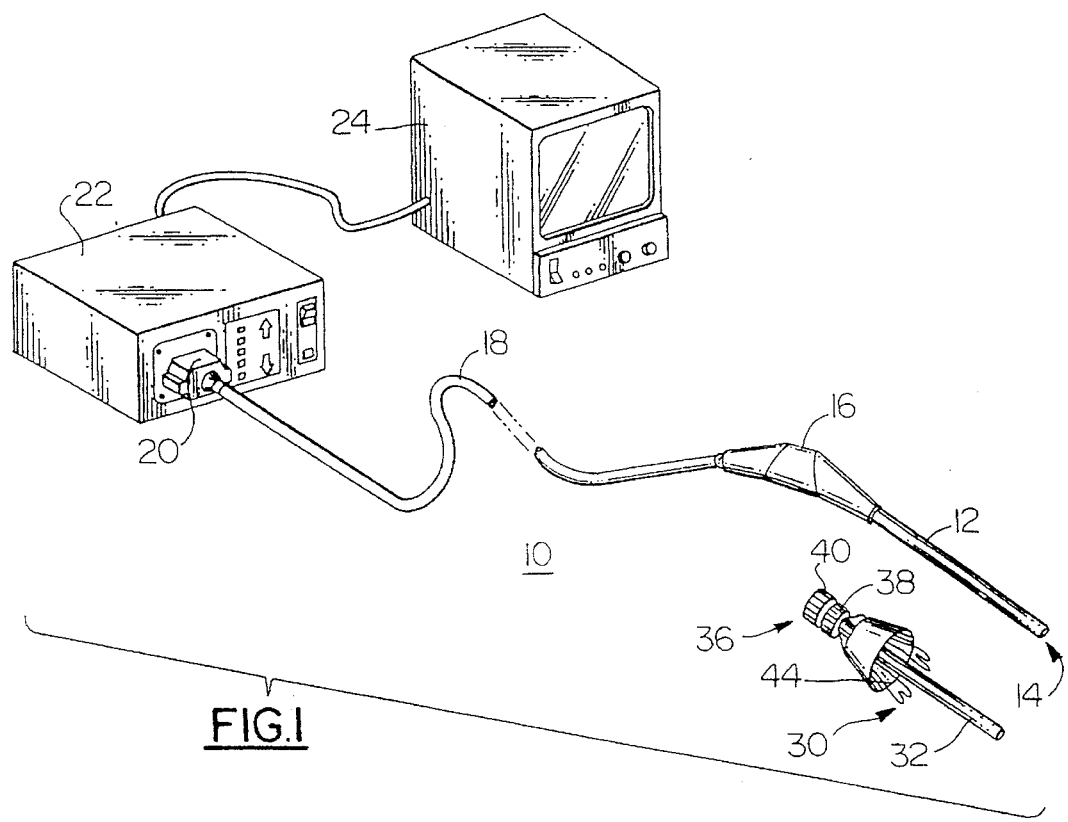
FIG. 1 is a perspective view of a video laparoscope and an associated sterile sheath and drape according to one embodiment of this invention.

With reference to the drawing and initially to FIG. 1, a laparoscope assembly 10 is shown to have an elongated rigid insertion tube 12, in this case a tube of stainless steel. At its distal tip 14, the insertion tube contains a video camera and associated focusing optics, as well as an optical conduit that brings illumination to a concealed target. The video camera forms an image of the target, and sends a video signal down through the insertion tube 12. A handle portion 16 is affixed onto the proximal end of the tube 12, and a flexible umbilical tube 18 extends from the handle portion 16 to a plug-in connector module 20, which in this case contains electronics for converting the signal, provided from the camera in the distal tip 14, to a standard-format video signal. The module 20 fits into a socket on a power supply and light unit 22. This unit 22 contains a wiring harness which also feeds the processed standard-format video signal to a monitor 24.

Figure 2:
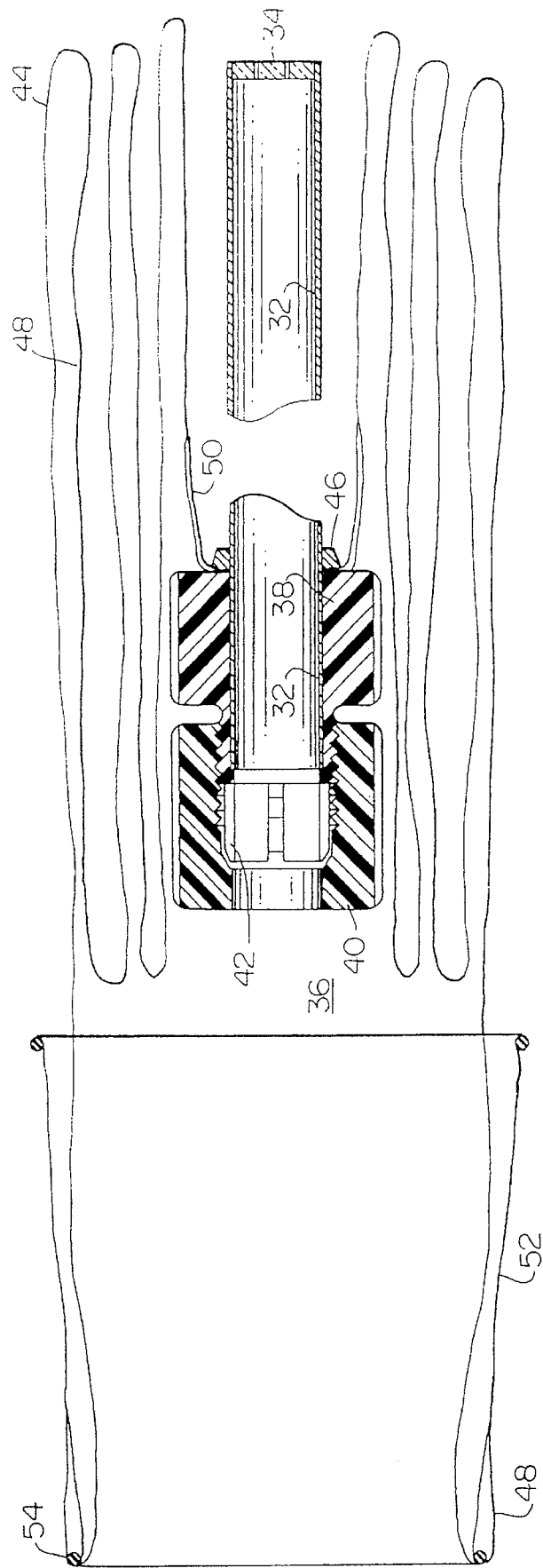
FIG. 2 is an enlarged sectional view of the sheath and drape of this embodiment.

A sterile sheath 30 for the insertion tube is shown with further reference to FIG. 2. The sheath 30 can be either disposable or reusable, in which case it is designed to be sterilizable. The sheath has an elongated cylindrical wall 32, here formed of thin-gauge stainless steel, with an inside diameter in this embodiment of about 10.1 mm. This sheath 30 is designed to fit onto a laparoscope insertion tube 12 having an outside diameter of about 10.0 mm. This provides a snug fit, but there is enough clearance to permit the insertion tube 12 to slide into the sheath 30.

At the distal end of the cylindrical wall 32 there is a front window or face plate 34 to permit the illumination from the light conduit optical fibers to pass to the target and to permit light from the target to reach the camera or other imager. At a proximal end of the sheath 30 there is a grip mechanism 36 here of a two-part construction. A female-threaded rear portion 38 fits into a male-threaded forward portion 40. Collet action squeezes the slotted proximal end 42 of the portion 40 inward for gripping the insertion tube 12.

As shown in FIG. 2, a sterile polyethylene film drape 44 in the form of a sleeve or tube is attached to the cylindrical wall 32 to unfold and pull back over the handle portion 16 and umbilical 18 to prevent contamination of these parts from contact with the patient's body fluids. This drape 44 is retained by a ring or hub member 46 attached to the distal side of the formed portion 40 of the grip 36. After use, the entire grip mechanism 36 can be removed from the proximal end of the cylindrical wall 32. Then after the sheath has been sterilized, a new sterile grip mechanism 36 and drape 44 can be installed for the next use.

As shown in FIG. 2 the polyethylene drape 44 has a main body 48 formed of clear 2 mil film, and a thick nose portion 50 at the distal end where the drape 44 is attached by means of the ring member 46.

The proximal end of the main body 48 is bonded to a generally cylindrical or frustoconic tube 52. This tube is made of a more-or-less rigid material, with open ends and annular stiffening ribs 54 and 56 at its proximal and distal ends. Preferably, the drape main body 48 is bonded onto an outer surface of the rigid tube 52.

Figure 3:
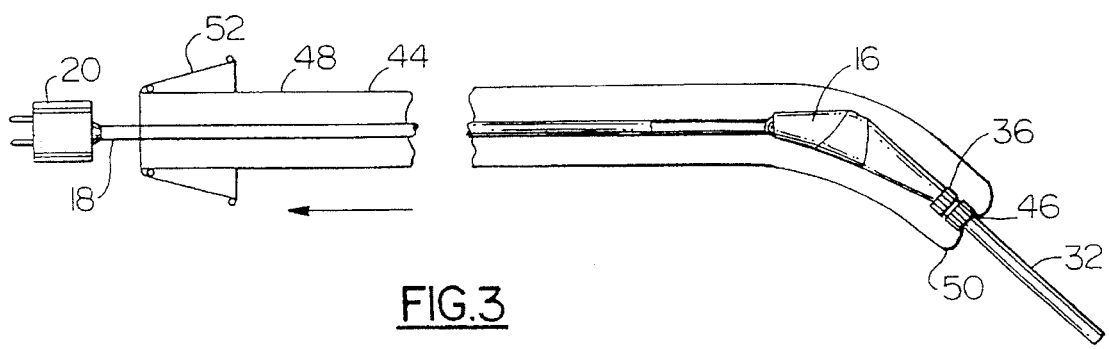
FIGS. 3 and 4 are simplified schematic views of the laparoscope and the sheath and drape, installed for surgical use and being removed after surgery, respectively.
Figure 4:
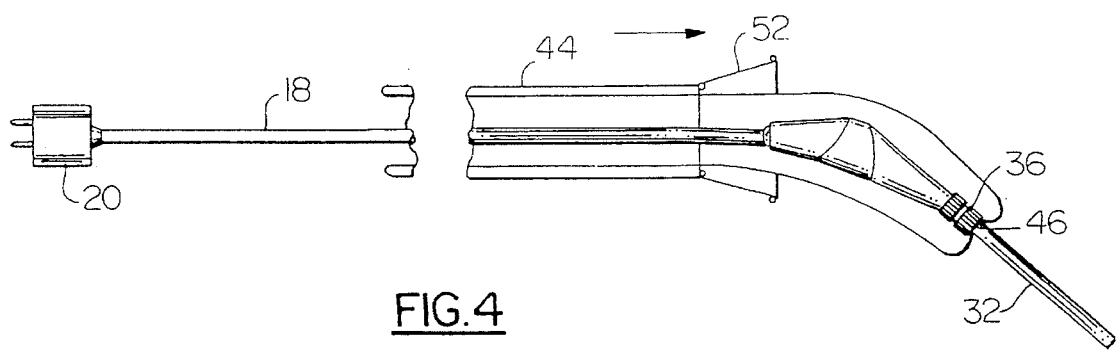

For storage, shipping, and installation, the drape 44 is folded axially back and forth as shown in FIG. 2, with the rigid tube 52 aligned on the outside. In this form the sheath 30 can be installed over the insertion tube 12 and the grip mechanism can be tightened. Then, prior to a surgical procedure, the drape 44 is opened out by grasping the rigid tube 52 and pulling it back over the handle 16 and umbilical 18, as shown in FIG. 3. This shields the entire probe from contamination during the procedure. Then, following surgery, the rigid tube 52 is grasped and is pulled all the way forward, as shown in FIG. 4. This uncovers the handle 16 and umbilical 18, and covers the entire sheath 30. This also reverses the drape 44, turning it inside out, so that the clean inner side is exposed on the outside surface, while the contaminated outer side is facing inward towards the contaminated surface of the sheath 30. Then the grip mechanism 36 can be loosened for removal of the sheath from the insertion tube.

As maintained earlier, the now-contaminated drape can be removed from the rigid tubular sheath, e.g., after a preliminary disinfection. Then, the rigid tubular sheath can be sterilized, and fitted with a new grip mechanism 36 and drape 44.

Of course, this drape can take on other forms, depending on the environment in which it is used. The type of material as well as its thickness, clarity, and other properties can be varied widely.

While this invention has been described in detail with reference to a preferred embodiment and a few selected alternative embodiments, it should be understood that the invention is not limited to these embodiments. Rather, many modifications and variations would present themselves to those of skill in the art without departing from the scope and spirit of this invention, as defined in the appended claims.

What is claimed is:

1. A method of cloaking a laparoscope with a sterile sheath for a surgical operation to minimize contamination to the laparoscope or to surgical personnel, wherein the laparoscope includes a rigid insertion tube of a predetermined outer diameter imaging means contained within a distal tip of the insertion tube for obtaining an image of a target and an elongated flexible umbilical to couple the insertion tube to illumination equipment; and wherein the sterile sheath includes a rigid tube with an inner diameter slightly greater than the outer diameter of the insertion tube and a sterile, generally tubular drape formed of a flexible membrane having a distal end attached to a proximal end of said rigid tube; the method comprising:

prior to surgery, sliding the tubular sheath onto the insertion tube; and drawing the drape proximally to enclose the insertion tube and the umbilical therewithin; and after surgery drawing the drape distally to cover the rigid tube and invert the drape so that any contaminants that have collected on it are contained on an inward facing surface of the drape;

and removing the sheath from the laparoscope insertion tube.

2. The method of claim 1, wherein said drape is initially disposed in a folded configuration in which the drape is folded back and forth axially over the rigid tube; and the step of drawing out said drape includes unfolding said drape into an elongated configuration.

3. The method of claim 1, further comprising the step of discarding said drape following the step of removing the sterile sheath.

4. The method of claim 3, further comprising replacing the contaminated drape with a fresh sterile drape.

5. A sterile sheath for a laparoscope which has a rigid insertion tube of a predetermined outer diameter, imaging means contained within a distal tip of the insertion tube for obtaining an image as viewed by the imaging means of a target, and an elongated flexible umbilical to couple said insertion tube to illumination equipment; the sterile sheath comprising a rigid tube with an inside diameter slightly greater than the outer diameter of the insertion tube for slidably fitting thereover and a transparent face plate at a distal tip of the rigid tube, and a sterile generally tubular drape formed of a flexible membrane having a distal end attached to a proximal end of said rigid tube, and being folded axially back and forth over the rigid tube, with the sterile sheath further comprising a gripping mechanism at a proximal end of said rigid tube, including tightening means for releasably gripping the insertion tube, wherein said gripping mechanism further includes a ring member on a distal end of said gripping mechanism retaining a distal end of said drape on said rigid tube, and wherein said drape has a main body of a predetermined film thickness and a nose portion of a greater film thickness adjacent said ring member, with said drape being free of external securing means along its length, such that after the sterile sheath is installed on said insertion tube for a surgical procedure, the folded drape is unfolded by drawing the same proximally to enclose said umbilical therewithin, and following a surgical procedure, the unfolded drape is inverted by drawing the same distally to ,cover the rigid tube and to contain within the drape any contaminants that have collected on it during said surgical procedure.

6. A sterile sheath for a laparoscope which has a rigid insertion tube of a predetermined outer diameter, imaging means contained within a distal tip of the insertion tube for obtaining an image as viewed by the imaging means of a target, and an elongated flexible umbilical to couple said insertion tube to illumination equipment; the sterile sheath comprising a rigid tube with an inside diameter slightly greater than the outer diameter of the insertion tube for slidably fitting thereover and a transparent face plate at a distal tip of the rigid tube, and a sterile generally tubular drape formed of a flexible membrane having a proximal end which is bonded to a substantially rigid tube member, a distal end attached to a proximal end of said rigid tube, and being folded axially back and forth over the rigid tube, with said drape being free of external securing means along its length, such that after the sterile sheath is installed on said insertion tube for a surgical procedure, the folded drape is unfolded by drawing the same proximally to enclose said umbilical therewithin, and following a surgical procedure, the unfolded drape is inverted by drawing the same distally to cover the rigid tube and to contain within the drape any contaminants that have collected on it during said surgical procedure.

7. The sterile sheath of claim 6 wherein said rigid tube member is frustoconic.

* * * * *